April 24, 1956 R. V. LINDQUIST Plant Pat. 1,471
ROSE PLANT
Filed May 23, 1955
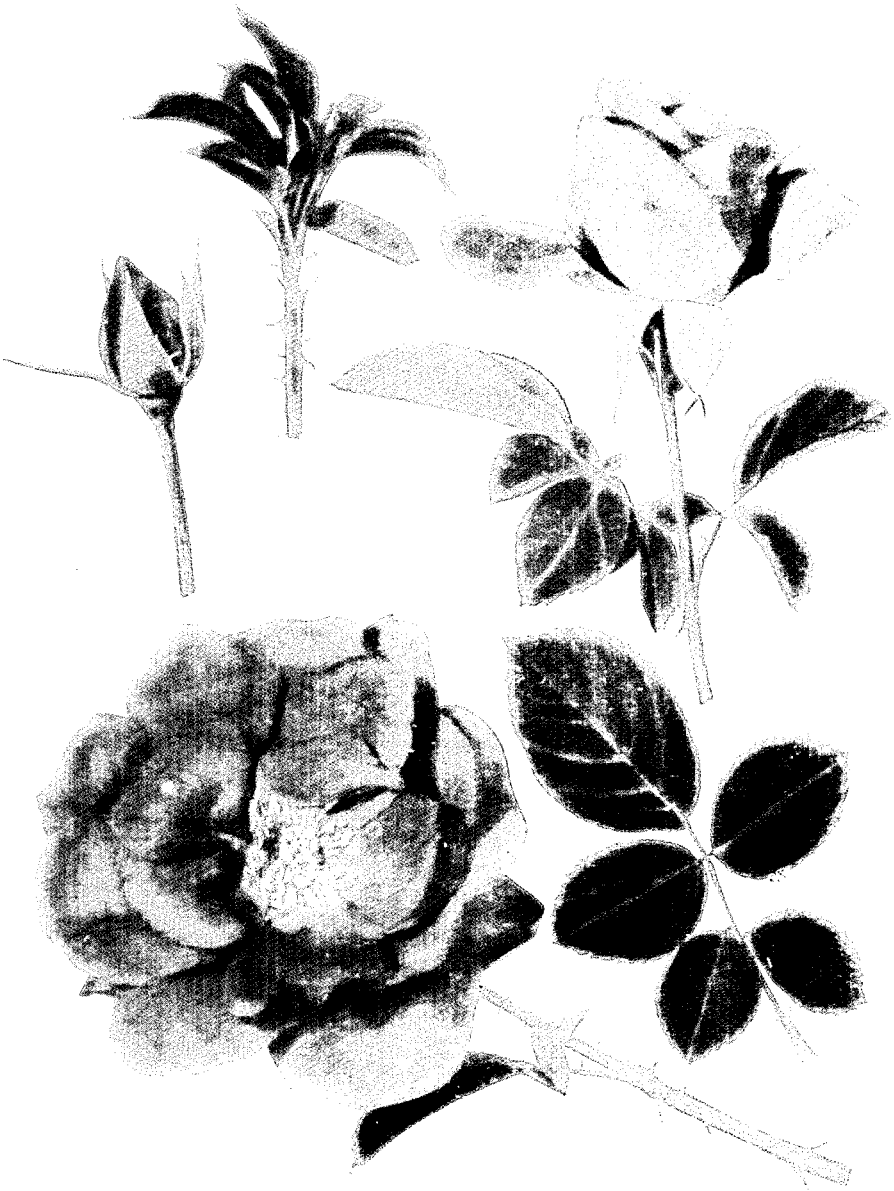
Inventor.
R. V. Lindquist
By: Robb & Robb
Attorneys.

United States Patent Office

Plant Pat. 1,471
Patented Apr. 24, 1956

1,471

ROSE PLANT

Robert V. Lindquist, Hemet, Calif., assignor to Hemet Wholesale, Hemet, Calif., a partnership Application May 23, 1955, Serial No. 510,595

1 Claim. (Cl. 47—61)

The present invention relates to a new and distinct variety of rose plant of the hybrid polyantha class, which was originated by me by crossing the variety known as "Improved Lafayette" (unpatented) with the variety "Peace" (Plant Patent No. 591).

As the result of this breeding, I have produced a new rose variety which is particularly characterized as to novelty by the distinctive Rose Red general color tonality of its flowers and by its ability to produce flowers in clusters on stems of medium to long length, as well as to produce flowers singly. A still further outstanding characteristic and distinctive feature of my new variety is its numerous thorns on the branches of the plant. These characteristics and distinctions definitely differentiate my new variety from its parents, as well as from all other varieties of its class of which I am aware.

Asexual reproduction of my new variety by budding, as performed at Hemet, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Ridgway's Color Standards and Nomenclature (hereinafter abbreviated as "Ridgway"), as indicated, except where color terms of ordinary dictionary significance are obvious:

Type: Bush; outdoor; seedling; for garden decoration.
Class:
*Botanic.*—Hybrid polyantha.
*Commercial.*—Grandiflora.
Breeding: Seedling.
*Seed parent.*—"Improved Lafayette."
*Pollen parent.*—"Peace."
Propagation: Holds its distinguishing characteristics through succeeding propagations by budding.

FLOWER

Locality where grown and observed: Hemet, California.
Flowers borne: Both singly and several to stem; in irregular clusters; on stems varying from medium length to long.
Quantity of bloom: Free, outdoors.
Continuity: Continuous during growing season.
Fragrance: Moderate. Nature—Tea.
Bud:
*Peduncle.*—Average length; average caliper; erect; rough; with numerous prickles. Color—Reddish Green.
*Before calyx breaks.*—Size—medium. Form—ovoid; with foliaceous appendages on the surface of the bud; with slender foliaceous parts extending beyond the tip of the bud equal to ¼ or more of its length.

*As calyx breaks.*—Color—near Rose Red, Plate 724, page 158 (Wilson).
*Sepals.*—Inner surface—with fine woolly tomentum. Margins—with few foliaceous appendages and gland-tipped cilia.
*As first petal opens.*—Size—average. Form—ovoid. Color: outside—near Rose Red, Plate 724/1, page 158 (Wilson); inside—near Rose Red, Plate 724, page 158 (Wilson).
*Opening.*—Opens up well; is not retarded from opening by hot, wet or dry weather.
Bloom:
*Size (when fully open).*—Average; from 3½ inches to 4 inches.
*Petalage.*—Double; from 20 to 25 petals, plus 1 to 3 petaloids; arranged regularly.
*Form.*—High-centered at first, but becoming somewhat flat; petals being at first somewhat rolled outward, but later becoming loosely rolled outward at maturity.
Petals:
*Texture.*—Thick; with inside velvety and outside satiny.
*Shape.*—Outside—round. Intermediate—round. Inside—nearly oval.

This description of a newly opened flower was made from a rose grown outdoors in the month of October, at Hemet, California:

Color:
*Outside petal.*—Outside surface—near Rose Red, Plate 724/1, page 158 (Wilson), with base near Canary Yellow, Plate 2/2, page 2 (Wilson). Inside surface—near Rose Red, Plate 724, page 158 (Wilson), with base near Canary Yellow, Plate 2/1, page 2 (Wilson).
*Intermediate petal.*—Outside surface—near Rose Red, Plate 724/2, page 158 (Wilson), with base near Canary Yellow, Plate 2/2, page 2 (Wilson). Inside surface—near Rose Red, Plate 724, page 158 (Wilson), with base near Canary Yellow, Plate 2/1, page 2 (Wilson).
*Inner petal.*—Outside surface—near Rose Red, Plate 724/2, page 158 (Wilson), with base near Canary Yellow, Plate 2/2, page 2 (Wilson). Inside surface—near Rose Red, Plate 724, page 158 (Wilson), with base near Canary Yellow, Plate 2/1, page 2 (Wilson).

This description was made from a rose that was open for 3 days outdoors in the month of October, at Hemet, California:

Color:
*Outside petal.*—Outside surface—near Rose Red, Plate 724/1, page 158 (Wilson), with base near Canary Yellow, Plate 2/2, page 2 (Wilson). Inside surface—near Rose Red, Plate 724, page 158 (Wilson), with base near Canary Yellow, Plate 2/1, page 2 (Wilson).
*Inside petal.*—Outside surface—near Rose Red, Plate 724/3, page 158 (Wilson), with base near Canary Yellow, Plate 2/2, page 2 (Wilson). Inside surface—near Rose Red, Plate 724/1, page 158, (Wilson), with base near Canary Yellow, Plate 2/1, page 2 (Wilson).
General color effect:
*Newly opened flower.*—Near Rose Red, Plate 724/1, page 158 (Wilson).
*3-days open.*—Near Rose Red, Plate 724, page 158 (Wilson).

Behavior: Drop off cleanly; affected by cold weather by deepening of the color at outside edge of petals.

Flower longevity: On bush in garden—3 or 4 days in October.

REPRODUCTIVE ORGANS

Stamens: Many; arranged regularly about pistils.

Filaments: Medium length. Color—near Rose Opal, Plate 022/1, page 110 (Wilson) at base, shading to near Orange Buff, Plate 507/1, page 133 (Wilson).

Anthers: Medium size; all open approximately at once. Color: upper side—near Orange Buff, Plate 507, page 133 (Wilson); under side—near Orange Buff, Plate 507/1, page 133 (Wilson).

Pollen: Moderate. Color—near Indian Yellow, Plate 6/2, page 6 (Wilson).

Pistils: Many; approximately 125 to 140 in number.

Styles: Moderately uneven; average length; average caliper; somewhat bunched.

Stigma: Color—near Orange Buff, Plate 507/1, page 133 (Wilson).

Ovaries: Usually mostly enclosed, but some protruding from calyx.

Hips: None.

Sepals: Falling soon; medium length; spear-shaped; recurved. Color: inside—near Light Fluorite Green, Plate XXXII (Ridgway); outside—near Bice Green, Plate XVII (Ridgway).

Seeds: None.

PLANT

Foliage:

*Leaves.*—Compound of usually 5 to 7; normal quantity; medium size; moderately heavy; somewhat leathery.

*Leaflets.*—Shape—oval, with apex mucronate. Base—round. Margin—serrate.

*Color.*—Mature: upper surface—near Dark Dull Yellow Green, Plate XXXII (Ridgway); under surface—near Bice Green, Plate XVII (Ridgway). Young: upper surface—near Elm Green, Plate XVII (Ridgway), shading to near Dark Corinthian Purple, Plate XXXVIII (Ridgway) at outside edge; under surface—near Corinthian Purple, Plate XXXVIII (Ridgway).

*Rachis (the supporting stem of the compound leaf).*—Average size. Upper side—grooved; with few stipitate glands on edges. Under side—moderately prickly; with some stipitate glands.

*Stipules.*—Medium length; medium width; with medium length points turning out at an angle of about 45°.

*Disease resistance.*—Mildly subject to mildew as compared with other varieties grown under comparable cultural conditions at Hemet, California.

Growth:

*Habit.*—Upright; moderately branched.

*Growth.*—Vigorous.

*Canes.*—From medium to heavy caliper.

*Main stems.*—Color—near Bice Green, Plate XVII (Ridgway). Large prickles—many; medium length; hooked slightly downward; with moderately narrow base. Color—near Cinnamon Brown, Plate XV (Ridgway). Small prickles—many. Color—near Cinnamon Brown, Plate XV (Ridgway). Hairs—none.

*Branches.*—Color—near Bice Green, Plate XVII (Ridgway). Large prickles—many; medium length; hooked slightly downward; with moderately narrow base. Color—near Cinnamon Brown, Plate XV (Ridgway). Small prickles—many. Color—near Cinnamon Brown, Plate XV (Ridgway). Hairs—none.

*New Shoots.*—Color—near Biscay Green, Plate XVII (Ridgway), shading to near Corinthian Purple, Plate XXXVIII (Ridgway). Large prickles—many; medium length; almost straight; with narrow base. Color—near Madder Brown, Plate XIII (Ridgway). Small prickles—many. Color—near Madder Brown, Plate XIII (Ridgway). Hairs—none.

I claim:

A new and distinct variety of rose plant of the hybrid polyantha class, substantially as herein shown and described, characterized particularly as to novelty by the distinctive Rose Red general color tonality of its flowers, its ability to produce flowers both singly and in clusters on stems from medium length to long, and the thorniness of its branches.

No references cited.